United States Patent [19]

Papa

[11] 4,184,486
[45] Jan. 22, 1980

[54] DIAGNOSTIC METHOD AND SENSOR DEVICE FOR DETECTING LESIONS IN BODY TISSUES

[75] Inventor: Lajos Papa, Hatvan, Hungary

[73] Assignee: Radelkis Elektrokemiai Muszergyarto Szovetkezet, Budapest, Hungary

[21] Appl. No.: 823,586

[22] Filed: Aug. 11, 1977

[51] Int. Cl.² ............................................. A61B 5/05
[52] U.S. Cl. .................................... 128/642; 128/734
[58] Field of Search ............. 128/2.1 R, 2.1 C, 2.1 E, 128/2.1 Z, 2 R, 2 E

[56] References Cited

U.S. PATENT DOCUMENTS

| | | | |
|---|---|---|---|
| 2,516,882 | 8/1950 | Kalom | 128/2.1 R |
| 2,637,316 | 5/1953 | Grez | 128/2.1 R |
| 2,763,935 | 9/1956 | Whaley et al. | 128/2.1 R |
| 3,083,706 | 4/1963 | Woodhouse | 128/2.1 E |
| 3,749,089 | 7/1973 | Derr | 128/2.1 E |

FOREIGN PATENT DOCUMENTS

| | | | |
|---|---|---|---|
| 667600 | 10/1929 | France | 128/2.1 R |
| 1381419 | 11/1964 | France | 128/2.1 R |

OTHER PUBLICATIONS

Ash, "Detecting Electrical Change in Cancer," Research Disclosure, No. 142, p. 14, Feb. 1976.

*Primary Examiner*—Lee S. Cohen

[57] ABSTRACT

Diagnostic method and sensor device for detecting the location and/or character of lesions in body tissues. Electrodes of different substances are put onto or into a tissue being tested, the electrodes are nearly short-circuited over a measuring device, and the current flowing through the terminals of the electrodes is measured. The measured value of the current is then compared with a control value measured in the same way on a piece of sound tissue. One embodiment of a sensor device that can be applied for the performance of the method comprises a pair of electrodes, made of different materials so as to have different contact potentials, the electrodes being coupled to an electric measuring instrument, e.g. an ammeter, one of the electrodes being a metal tube such as a medical syringe, whereas the other electrode is enveloped by an insulating material and fixed inside the metal tube. The other electrode can be made of magnesium, and its active surface is preferably arranged in the front plane of or outside the metal tube. Another embodiment of the device is made of a medical sample excision spoon wherein two arm parts of the spoon constitute the electrodes, both being fixed to an insulating material and provided with terminals that are coupled to the ammeter.

3 Claims, 3 Drawing Figures

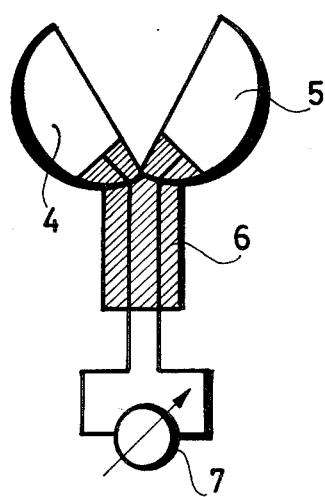
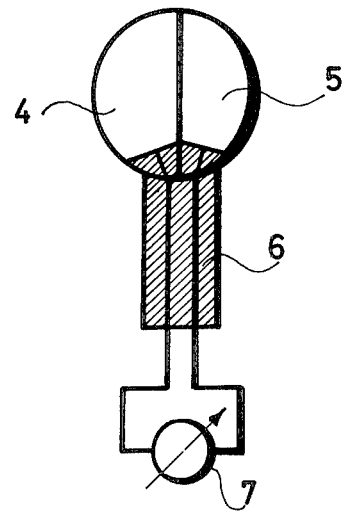
FIG. 2  FIG. 3
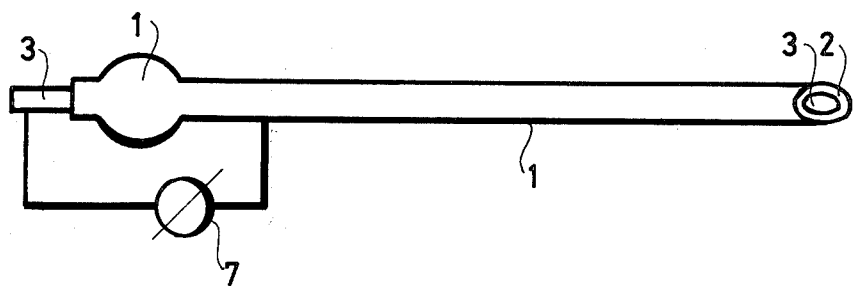
FIG. 1

DIAGNOSTIC METHOD AND SENSOR DEVICE FOR DETECTING LESIONS IN BODY TISSUES

The invention relates to a method and a device for detecting the location and/or character of a lesion in body tissues, in the course of which electrodes are put onto or into the tissue, and an electric measuring device is connected to the electrodes in order to measure the electric characteristics of the tissue.

Under the title "The modification of the electrolyte equilibrium in the malignant proliferation of the skin", a survey was published in September, 1969 in the medical journal Magyar Onkologia (Hungary) on research accomplishments and literature sources concerning the establishing of lesions in body tissues.

The publications disclose the so called resistance-measuring /impedance-measuring/ method for establishing/malignant/lesions in body tissues. One of the most up-to-date variants of this method consists in that a square-wave pulse is supplied to the surface of the deformed tissue, the pulse passing through a tissue to the sensor electrode and appearing on the screen of an oscilloscope coupled to an electrode, and this signal is then evaluated. The displayed waveshape is characteristic of the impedance of the body tissue. This is suitable for diagnostically establishing lesions on the surface of the tissue.

It is disadvantageous that its application is restricted to the detection of surface lesions; even if the electrodes are introduced into the body or its cavities, no reliable, valuable measurement can be obtained since it is the laminar cuticle the decay of which causes a change in the capacitive component of the impedance.

The examination of the body tissue and especially the methods applied according to the prior art in the field of diagnosis of malignant tumors are rather sophisticated and involve a waste of time. The minimum duration of a conventional histological examination amounts up to 24 hours. Although the examination of quick-freezing excisions can be performed within only 10 minutes or so, such a method can only be performed successfully by experts of special skill in this field since the quick-freezing process destroys the cells.

A well-known diagnostic method is one that utilizes radioactive isotopes but for this purpose expensive equipment is needed, and furthermore there is the disadvantage of radiation damage.

Thermometric examinations are not suitable because of their lack of reliability.

Supersonic examinations are apt to detect the location of damaging tissue lesions but no information can be obtained concerning the character of the lesions.

The uncertainty in establishing a tumor is specified for X-ray examinations by 17,5%, for gastroscopy by 39%, for cytology by 21%.

It has already been mentioned that the resistance or conductivity measurement according to the prior art is suitable only for the detection of lesions appearing at the surface of the skin or in tissues directly covered by cuticles; the measured value is affected by many factors such as the structure of the tissue, the state of the surface of the tumor/intact or not/etc.

A solution has been sought for making it possible to establish the location and/or the character of a lesion in body tissues by a diagnostic method and by a sensor device suitable even in cases when the tumor is embedded in the tissue of the body, and that in a quick and reliable manner without the need of a sample excision.

The invention is based on the concept that such a diagnostic method can be found if one utilizes a special feature of the tissue, viz. the fact that the electrolyte content of malignant tissues is of a higher value than that of sound tissues. It has been conceived that two electrodes of different materials - if put into the tissue - may be considered a primary cell that supplies a potential that in itself is not characteristic of the electrolyte content of the tissue but the loadability of the primary cell is dependent on the electrolyte content of the tissue.

The method according to the invention is performed by putting electrodes of different materials onto or into the body tissues, nearly short circuiting the electrodes over a measuring device, and measuring the current that flows through the electrode terminals.

It is suggested to compare the measured value of the current that flows between the electrodes with a value measured in the same manner on a piece of sound tissue.

The inventive sensor device comprises an electric ammeter, and one of the electrodes coupled to the input of the meter consists in a metal tube such as a medical syringe, whereas the other electrode is enveloped by an insulating material and fixed inside the metal tube. The other electrode can be made e.g. of magnesium or carbon, and its active surface is preferably arranged in the front plane of or outside the metal tube.

A further inventive sensor device comprises an electric ammeter, and the measuring electrodes are embodied by different parts of a sample excision spoon, each part being fixed to an insulating material and coupled over terminals to the meter.

It is an advantage of the method and the sensor device according to the invention that the location and the character of tumors embedded into sound tissues can immediately and reliably be established without the need of making sample excisions. This way it is possible to detect lesions also by endoscopy, puncture or biopsy.

The subject matter of the invention will now be set forth more particularly with reference to the accompanying drawing showing preferred embodiments of the sensor device, and wherein FIG. 1 shows a sensor device made of a medical syringe;

FIG. 2 shows a sensor device made in the shape of a sample excision spoon with shanks or arms open; whereas;

FIG. 3 shows the sensor device appearing in FIG. 2 but with closed shanks.

It can be seen in FIG. 1 that the diagnostic sensor device according to the invention is made by utilizing a medical syringe. One of the electrodes of the sensor device is the syringe 1 itself which is made of metal. Inside the tube of the syringe 1 an inner electrode 3 is arranged that is enveloped by insulating material 2. The inner electrode 3 is of another material than the syringe 1, i.e. their contact potentials are different as compared with that of hydrogen. If the syringe 1 is made of stainless steel, the inner electrode 3 can e.g. be made of magnesium or carbon. The material 2 is preferably Teflon. The active surface of the inner electrode 3 can be arranged in the same plane with the surface of the insulating material 2 and the end of the syringe but it can stick out of the syringe as well. The syringe 1 and the electrode 3 are coupled to input terminals of an electric measuring instrument, preferably an ammeter 7.

FIGS. 2 and 3 show another embodiment of the diagnostic sensor device according to the invention. This device consists essentially of a sample excision spoon as it is known according to the prior art, wherein two arm parts 4, 5 of the spoon are fixed on an insulating part 6. The parts 4, 5 are made of different metals the contact potentials of which are again different, as compared with that of hydrogen, and they are provided with terminals led through the isolating part 6 and again coupled to the input terminals of the ammeter 7. The arm parts 4, 5 are fixed to the insulation 6 in a manner that allows them to functionally cooperate as an excision spoon to contact the tissues being tested.

Either of the sensor devices as set forth above can be applied for performing the diagnostic method according to the invention. The essence of the method consists in that electrodes of different materials are put onto or into a body tissue, the electrodes are then short-circuited over a measuring device, and the current flowing across the terminals of the electrodes is measured, whereupon the measured current value is compared with a control value measured in the same way on a piece of sound tissue.

The method is based on the phenomenon that the electrolyte content of malignant tissues is higher than that of sound tissues. The electrolyte content is utilized as the electrolyte of a primary cell constituted by the electrodes introduced into the tissue. The loadability of the primary cell is characteristic of the electrolyte content. Theoretically, the voltage of the primary cell is independent of the electrolyte content. However in practice this value shows some dependence on the electrolyte content, even without an external load, which can be explained by that the internal conductivity of the body itself constitutes a load on the primary cell, that is established within the tissue of the body. This load effect is determined to a great measure by the dimensions and arrangement of the electrodes, by the volume of the tissue surrounding the electrodes, the electrolyte content etc.

The uncertainty caused by the internal conductivity of the body is compensated if the electrodes are nearly short-circuited across the measuring device. The short-circuit state shall be approximated to such a degree that a substantially greater current shall flow in the external circuit, coupled to the measuring device, than the load current flowing within the tissue of the body that surrounds the electrodes. The internal load current is substantially diminished if the electrodes are shortcircuited in the external circuit since the potential difference between the electrodes is also substantially diminished/-there remains only the voltage drop over the ammeter/.

The electrodes can be made of any firstclass conductor/metal/as long as they are different. The emf of the primary cell is dependent on the distance of the two metals from each other on the contact potential scale; the greater the distance the greater the voltage drop that can be permitted over the ammeter 7.

The sensitivity of the meter 7 coupled between the electrodes is chosen dependent on the material and the dimensions of the electrodes. If, e.g., the sensor device as shown in FIG. 1 has an external electrode 1 of stainless steel, and the diameter of the tube amounts 1 mm, whereas the inner electrode consists of magnesium and the active surface is a plane of 0.8 mm diameter, then the sound mycoderm of the stomach effects a current of at least 130–140 $\mu$A whereas a stomach adenocc. causes an increase of the current up to 220–230 $\mu$A. If one increases the active surface of the magnesium electrode, a proportional increase of the galvanic current can be obtained that is established in the tissue.

The method according to the invention can be applied in the field of skin tumor diagnostics, laryngology, gynaecology, and combinable endoscopic examinations. The method is suitable not only for the detection of permanent lesions in the tissues but even transitional changes in the state of the tissue can be detected and, thus, quick modifications in the process of life can be recognized, such as the prospective date of a childbirth or a danger menacing a foetus, by examining the surface of the cawl.

The method can be applied in order to detect a state preceding cancerosis in body tissues. The method makes it possible to draw conclusions concerning the state of the space inside a cell/e.g. loss of fluid in case of internal haemorrhage, inflammatory oedema etc. by examining the surface mycoderms/in the mouth, on the tongue/. The time necessary to make a diagnosis - if applying this method - is diminished from hours to seconds, and the result is even more exact than in case of microscopic examinations. If standardizing the electrodes and the measuring conditions, the malignus process can also be characterized by the absolute value of the current.

the location of the lesion in the tissue of the body can e.g. be established by inserting the electrodes in sequence at different points into the tissue and reading the current values the change of which shows the boundaries of the malignant tissue.

What we claim, is:

1. A diagnostic method for detecting the location and/or character of a lesion in body tissues, comprising the steps of: placing a pair of electrodes in contact with the tissue being tested; connecting an electric measuring device to the electrodes; measuring electric characteristics of the tissue relative to the current that flows through the electrodes; almost short-circuiting the electrodes through the measuring device; and determining from the current through the electrodes whether the tissue is sound or has a lesion therein.

2. The method as defined in claim 10, wherein said determining step includes comparing the measured value of the current through the electrodes with a control value measured in the same manner on a piece of sound tissue.

3. A diagnostic sensor device for detecting the location and/or character of a lesion in body tissues, comprising: an electric measuring ammeter; and a pair of electrodes made of different materials that have different contact potentials as compared to that of hydrogen; said electrodes being connected to respective input terminals of said ammeter; wherein said electrodes are in the form of respective arms of a medical sample excision spoon, said arms being fixed to an insulating material in a manner that allows them to functionally cooperate as an excision spoon to contact the tissues being tested.

* * * * *